United States Patent
Wang et al.

(10) Patent No.: US 12,305,978 B2
(45) Date of Patent: May 20, 2025

(54) MICROCRACK-BASED STRAIN SENSING ELEMENT, PREPARATION METHOD AND USE THEREOF

(71) Applicant: SOOCHOW UNIVERSITY, Suzhou (CN)

(72) Inventors: Qian Wang, Suzhou (CN); Zezhong Lu, Suzhou (CN); Kejun Wang, Suzhou (CN); Lei Gao, Suzhou (CN); Cheng Fan, Suzhou (CN); Lei Zhang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 419 days.

(21) Appl. No.: 17/799,642

(22) PCT Filed: Aug. 10, 2021

(86) PCT No.: PCT/CN2021/111707
§ 371 (c)(1),
(2) Date: Aug. 12, 2022

(87) PCT Pub. No.: WO2022/247018
PCT Pub. Date: Dec. 1, 2022

(65) Prior Publication Data
US 2024/0027178 A1    Jan. 25, 2024

(30) Foreign Application Priority Data
May 26, 2021 (CN) .......................... 202110578601.0

(51) Int. Cl.
*G01L 1/22*     (2006.01)
*A61B 5/00*     (2006.01)
*G01B 7/16*     (2006.01)

(52) U.S. Cl.
CPC .............. *G01B 7/18* (2013.01); *A61B 5/6824* (2013.01); *G01L 1/2293* (2013.01); *A61B 2562/0261* (2013.01)

(58) Field of Classification Search
CPC .......... A61B 5/6824; A61B 2562/0261; G01L 1/2293; G01L 1/005
See application file for complete search history.

(56) References Cited

FOREIGN PATENT DOCUMENTS

| CN | 1924564 A | 3/2007 |
|---|---|---|
| CN | 105627905 A | 6/2016 |

(Continued)

*Primary Examiner* — Jamel E Williams
*Assistant Examiner* — Alex T DeVito
(74) *Attorney, Agent, or Firm* — SZDC Law PC

(57) ABSTRACT

The invention discloses a microcrack-based strain sensing element and a preparation method and use thereof. The microcrack-based strain sensing element includes a substrate layer, a metal film, a protective layer, an output electrode, and a packaging layer. The metal film is arranged on the substrate layer. The metal film is formed by deposition of two metal materials. The metal film is provided with a patterned crack structure. The protective layer is arranged on the metal film. The output electrode is connected to the metal film for outputting an electrical signal. The packaging layer is arranged on the protective layer. Compared with existing crack preparation technologies, the preparation method of the microcrack-based strain sensing element of the invention has higher-precision crack controllability, does not affect the service life of cracks, and achieves more optimized actual operation. The microcrack-based strain sensing element has the advantages of high sensitivity, wearable performance and miniaturization.

8 Claims, 4 Drawing Sheets

(56) References Cited

FOREIGN PATENT DOCUMENTS

| | | | |
|---|---|---|---|
| CN | 105783697 A | | 7/2016 |
| CN | 109900394 A | | 6/2019 |
| CN | 110450481 A | | 11/2019 |
| CN | 211401071 U | | 9/2020 |
| KR | 20170063335 A | * | 6/2017 |
| KR | 20190091876 A | | 8/2019 |

* cited by examiner

MICROCRACK-BASED STRAIN SENSING ELEMENT, PREPARATION METHOD AND USE THEREOF

This application is the National Stage Application of PCT/CN2021/111707, filed on Aug. 10, 2021, which claims priority to Chinese Patent Application No. 202110578601.0, filed on May 26, 2021, which is incorporated by reference for all purposes as if fully set forth herein.

FIELD OF THE INVENTION

The invention relates to the technical field of micro-intelligent electronics, and specifically to a microcrack-based strain sensing element and a preparation method and use thereof.

DESCRIPTION OF THE RELATED ART

Conventional mechanical quantity sensors cannot meet the requirements of low power consumption, high stability, miniaturization, high precision, high mobility and other excellent performance, which are often the key elements of sensors in some fields that require high sensor performance, such as the field of wearable electronics, medicine, etc. Conventional wearable smart devices are generally non-flexible, and can be applied to certain parts only. With the development of flexible electric-conducting technologies, the emergence of flexible wearable smart devices has become possible. Flexible sensors are the core components of wearable smart devices. Existing methods for preparing flexible microcrack sensors have problems such as insufficient precision and affecting the service life of the sensor.

SUMMARY OF THE INVENTION

Therefore, a technical problem to be solved by the invention is to overcome the shortcomings of mechanical quantity sensors such as insufficient sensitivity, excessive size, and insufficient mobility in the prior art; and solve the problems such as insufficient precision and affecting the service life of the sensing element of the conventional methods for preparing crack-based strain sensors.

In order to solve the above technical problem, the invention provides a microcrack-based strain sensing element, including: a substrate layer, a metal film, a protective layer, an output electrode, and a packaging layer. The metal film is arranged on the substrate layer. The metal film is formed by deposition of two metal materials. The metal film is provided with a patterned crack structure. The protective layer is arranged on the metal film. The output electrode is connected to the metal film and configured to output an electrical signal. The packaging layer is arranged on the protective layer.

In an embodiment of the invention, a material of the substrate layer is selected from a film of polyimide (PI), polyethylene terephthalate (PET), polyvinyl chloride (PVC), nylon (PA), or cast polypropylene (CPP) material.

In an embodiment of the invention, the metal film layer is a film formed by deposition of a gold (Au) film and a chromium (Cr) phase, wherein gold (Au) can be replaced with a metal material selected from platinum (Pt), silver (Ag), and copper (Cu).

In an embodiment of the invention, a raw material of the protective layer is prepared by mixing and stirring an epoxy resin A glue and an epoxy resin B glue at a weight ratio of 3:1.

In an embodiment of the invention, a raw material of the packaging layer is prepared by mixing and stirring a polydimethylsiloxane (PDMS) sample liquid with water at a weight ratio of 10:1.

The invention also provides a method for preparing the microcrack-based strain sensing element, including the following steps:
(1) fabricating a coating template with a corresponding hollow shape according to a shape of a required sensing element, placing the coating template on a substrate layer, and coating a metal film layer formed by deposition of two metal materials on the substrate layer;
(2) fabricating a protective layer template with a pattern of the corresponding hollow shape according to a required crack density and position, and spray-coating a release agent;
(3) fixing the protective layer template to a surface of the metal film layer, and brush-coating a raw material of a protective layer on the protective layer template;
(4) demolding after curing of the protective layer, and arranging an output electrode to obtain a sample sheet;
(5) spin-coating a raw material of a packaging layer on a surface of the sample sheet; and
(6) bending and stretching the metal film layer to obtain a patterned crack structure on a surface of the metal film layer.

In an embodiment of the invention, the coating template includes a hollow part, and two ends of the hollow part are each provided with a protruding part.

In an embodiment of the invention, the protective layer template includes rectangular hollow grooves spaced apart from each other.

In an embodiment of the invention, the patterned crack structure is an array of cracks on the surface of the metal film layer, and the cracks are located between the protective layers arranged at intervals on the surface of the metal film layer.

The invention provides use of the microcrack-based strain sensing element or the method in the medical field.

The technical solution of the invention has the following advantages compared to the prior art:

According to the microcrack-based strain sensing element and the preparation method and use thereof of the invention, the microcrack-based strain sensing element has higher sensitivity of mechanical quantity sensing, mobility, wearability, and miniaturization than existing mechanical quantity sensor technologies. Compared with existing crack preparation technologies, the method for preparing microcracks by controllable patterning based on the template method has higher-precision crack controllability, does not affect the service life of cracks, and achieves more optimized actual operation. The microcrack-based strain sensing element has the advantages of high sensitivity, wearable performance, miniaturization and the like, and can be widely applied to the medical field.

BRIEF DESCRIPTION OF THE DRAWINGS

To make the content of the invention more comprehensible, the invention will be described in further detail below according to specific embodiments of the invention and in conjunction with the accompanying drawings, wherein.

DETAILED DESCRIPTION OF THE PREFERRED EMBODIMENTS

The invention will be further described below in conjunction with the accompanying drawings and specific embodiments, so that those skilled in the art can better understand and implement the invention, but the embodiments described are not intended to limit the invention.

Embodiment 1

This embodiment provides a microcrack-based strain sensing element, including: a substrate layer, a metal film, a protective layer, an output electrode, and a packaging layer. The metal film is arranged on the substrate layer. The metal film is formed by deposition of two metal materials. The metal film is provided with a patterned crack structure. The protective layer is arranged on the metal film. The output electrode is connected to the metal film and configured to output an electrical signal. The packaging layer is provided on the protective layer.

Specifically, the substrate layer carries the bottom of the sensing element, and needs to have mechanical properties such as flexibility, toughness, and wear resistance. the substrate is selected from: a film of polyimide (PI), polyethylene terephthalate (PET), polyvinyl chloride (PVC), nylon (PA), or cast polypropylene (CPP) material.

Specifically, the metal film layer is spray-coated on the substrate layer. Generally two metal materials need to be deposited to ensure a good bonding effect with the substrate layer. Patterned cracks are formed on the metal film layer as core elements of the sensor. The metal film layer is a film formed by deposition of a gold (Au) film and a chromium (Cr) phase, wherein gold (Au) can be replaced with a metal material selected from platinum (Pt), silver (Ag), and copper (Cu).

Specifically, the protective layer is brush-coated on the metal film by using a laser-cut template, and the neutral layer of the material is controlled to control crack patterning. A raw material of the protective layer is prepared by mixing and stirring an epoxy resin A liquid and an epoxy resin B liquid at a weight ratio of 3:1.

Specifically, the packaging layer is spin-coated on the metal film and the protective layer to protect the cracks on the cracked metal layer from being damaged by external environmental pollution. A raw material of the packaging layer is prepared by mixing and stirring a polydimethylsiloxane (PDMS) sample liquid with water at a weight ratio of 10:1.

Embodiment 2

Figure 1:
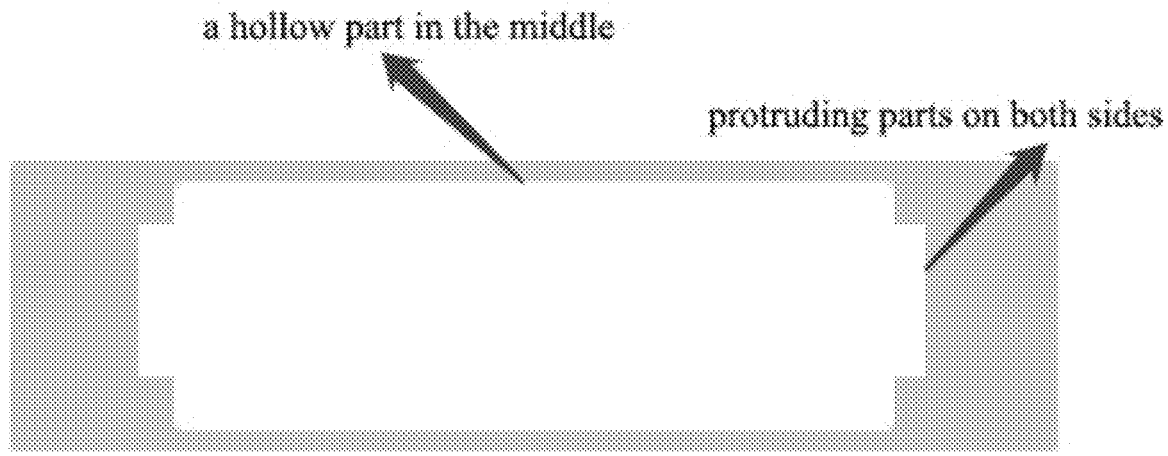
FIG. 1 is a schematic diagram of a coating template according to an embodiment of this application.

This embodiment provides a method for preparing the microcrack-based strain sensing element, including the following steps:

Step 1: A stainless steel sheet with a thickness of 3.5 cm×5.3 cm×0.01 cm is taken, and cut into a shape by laser cutting to fabricate a coating template. As shown in FIG. 1, a hollow part in the middle is used to form an expected shape during coating, and protruding parts on both sides are to facilitate the formation of output electrode lines.

Step 2: A 3.5 cm×5.3 cm PET film with a thickness of 0.025 mm is cut. The specimen is cleaned using a KH-100E ultrasonic cleaner and blow dried.

Step 3: A 3.5 cm×5.3 cm×1 cm glass slide is taken. First, a layer of ethanol is spray-coated on a surface of the glass slide; then the treated PET film is laid flat on the surface of the glass slide. It is to be noted that one end of the PET film should touch the glass slide first, then the PET film is slowly put down to prevent formation of bubbles, and afterward, the coating template fabricated in the step 1 is placed on the PET film and fixed with a transparent adhesive to prevent splashing during the spraying of metal.

Step 4: A metal layer is coated on the PET film using an SN201102003 high-vacuum magnetron coating equipment from the Suzhou Institute of Nano-tech and Nano-bionics, the Chinese Academy of Sciences, with the targets used being Cr and Au. To be specific, a 5 nm adhesive layer is first deposited with the Cr target, and then a 50 nm Au layer is deposited. Deposition parameters include: a vacuum degree of $5 \times 10^{-4}$ Pa, a power of 200 W, and a sputtering rate of 1 A/s.

Figure 2:
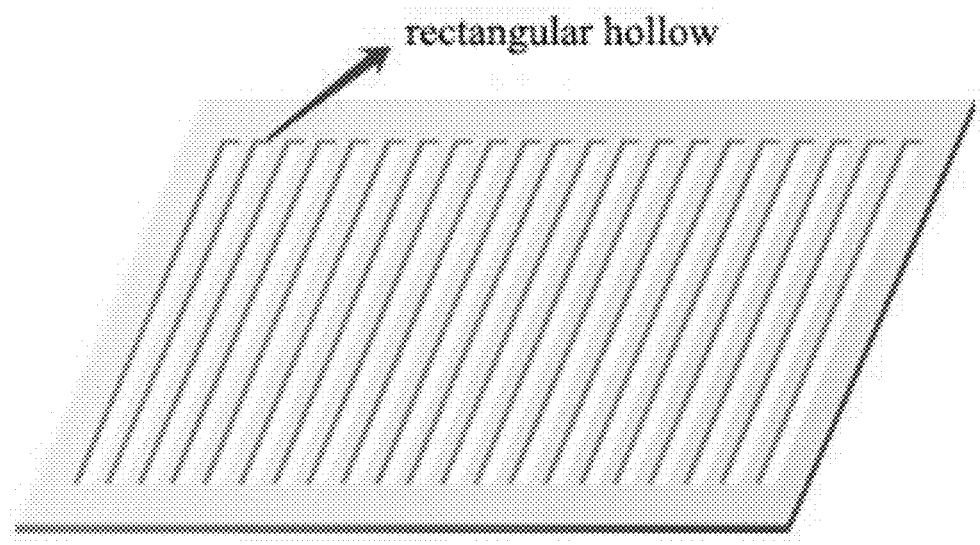
FIG. 2 is a schematic diagram showing laser cutting of a protective layer template according to an embodiment of this application.

Step 5: A stainless steel with a thickness of 3.5 cm×5.3 cm×0.01 cm is taken, and a hollow shape including rectangles arranged at intervals is designed according to a crack position and density requirement. As shown in FIG. 2, the hollow position is the position where cracks are formed. The stainless steel sheet is cut by laser cutting according to the designed shape, and a release agent is spray-coated on the stainless steel sheet to prepare a protective layer template.

Step 6: An epoxy resin A liquid and an epoxy resin B liquid are mixed at a weight ratio of 3:1, and stirred for 10 minutes using a DF-101S magnetic stirrer. Then the sample liquid is poured into a petri dish of 80 mm×80 mm, and vacuumed in a vacuum oven for 2 h to remove air bubbles.

Step 7: The vacuumed epoxy resin sample liquid is heated at 60° C. on a V-1515 heating table until the sample liquid is semi-cured.

Step 8: When the epoxy resin sample liquid reaches a certain viscosity, the protective layer template is placed on the PET-Au layer prepared in the step 4 and fixed using an electromagnet, the epoxy resin sample liquid is brush-coated on the protective layer template, and wait for curing.

Step 9: After curing of the protective layer, demolding is carried out, and electrode lines are arranged on protrusions at both ends of the PET-Au layer, with a conductive silver paste being used as a binder.

Step 10: A PDMS (Dow Corning) sample liquid is mixed with water at a weight ratio of 10:1, stirred for 10 minutes using a DF-101S magnetic stirrer, and then dried in a vacuum oven for 2 h.

The PDMS sample liquid is introduced into a KW-4B spin coater, and spin-coated onto the surface of the sample sheet prepared in the step 9 to serve as a packaging layer to protect the sample sheet from being polluted by the external environment.

Figure 3:
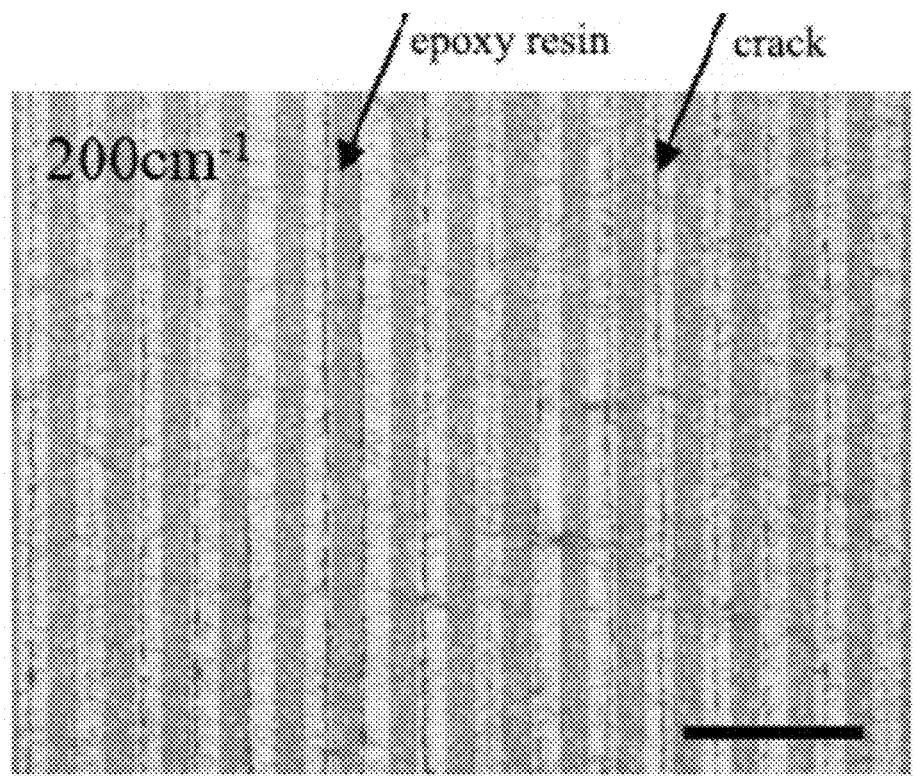
FIG. 3 is a schematic diagram of a microcrack array according to an embodiment of this application.
Figure 4:
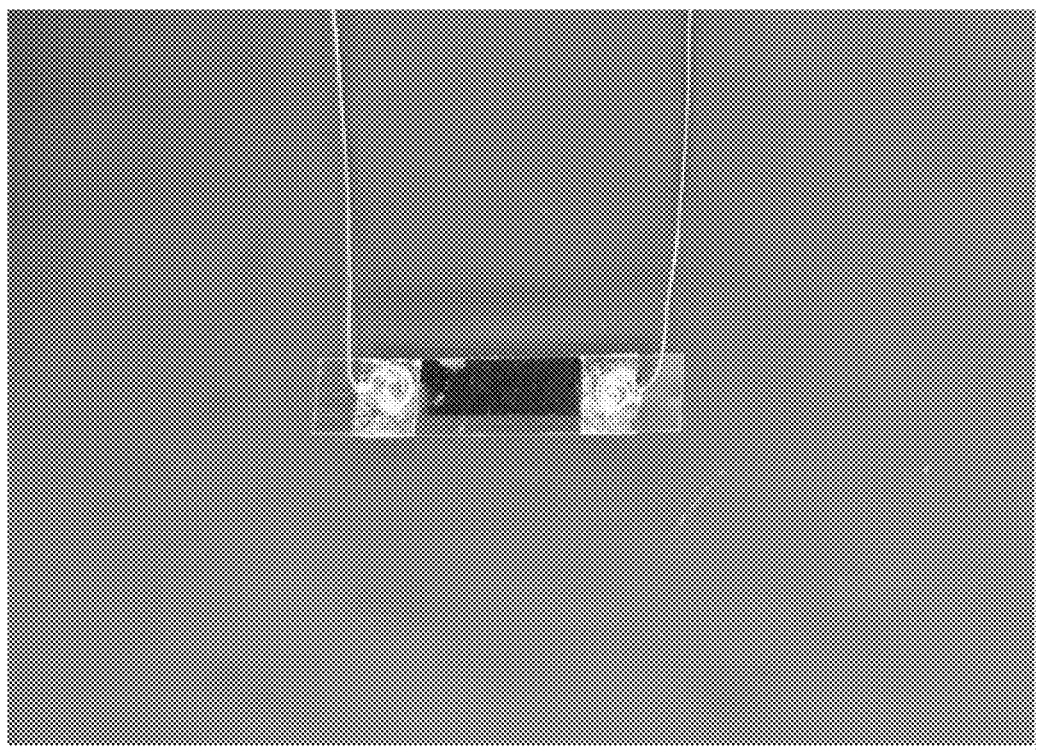
FIG. 4 is a schematic diagram of a microcrack-based strain sensing element according to an embodiment of this application.

Step 11: The metal film layer part of the sample sheet prepared in the step 10 is repeatedly bent and stretched on a round bar with a fixed radius of curvature ($\rho$), for example, $\rho=2$ mm. This operation can be implemented using an existing round bar stretching equipment, or manually, or may be implemented periodically and repeatedly using other stretching equipment, so that a microcrack array shown in FIG. 3 can be obtained between the two epoxy resin layers arranged at intervals on the surface of the metal film. A prepared microcrack sensor is shown in FIG. 4.

Embodiment 3

This embodiment provides use of a microcrack sensing element in the field of human physiological signal detection, including:
  closely attaching the microcrack-based strain sensing element to the chest of a human body, connecting electrode lines at both ends of the sensor to a multimeter, and recording a resistance value of the sensing element in a breathing process of the human body at a fixed frequency;
  processing the recorded resistance data through relative resistance ($\Delta R/R0$) calculation to obtain a breathing waveform with time as the abscissa, and analyzing a physiological condition or sleep quality of the human body during the recording period according to the waveform; and
  attaching the microcrack sensing element to a wrist of the human body, connecting the electrode lines at both ends of the sensor to a multimeter, and processing relative resistance data in real time using software to output a pulse detection curve with time as the abscissa in real time, where a main wave, a tidal wave, and a revival wave in the pulse waveform cycle can be distinguished from the curve, which can reflect a patient's heart rate during clinical surgery in real time, so as to determine the patient's physiological condition.

Further, the method of outputting a pulse detection curve in real time in the practical application of the flexible controllable microcrack sensing element in the field of human physiological signal detection can also be used for monitoring the breathing status of the human body in real time.

Embodiment 4

This embodiment provides an example of applying a microcrack sensing element to medical detection.

Figure 5:
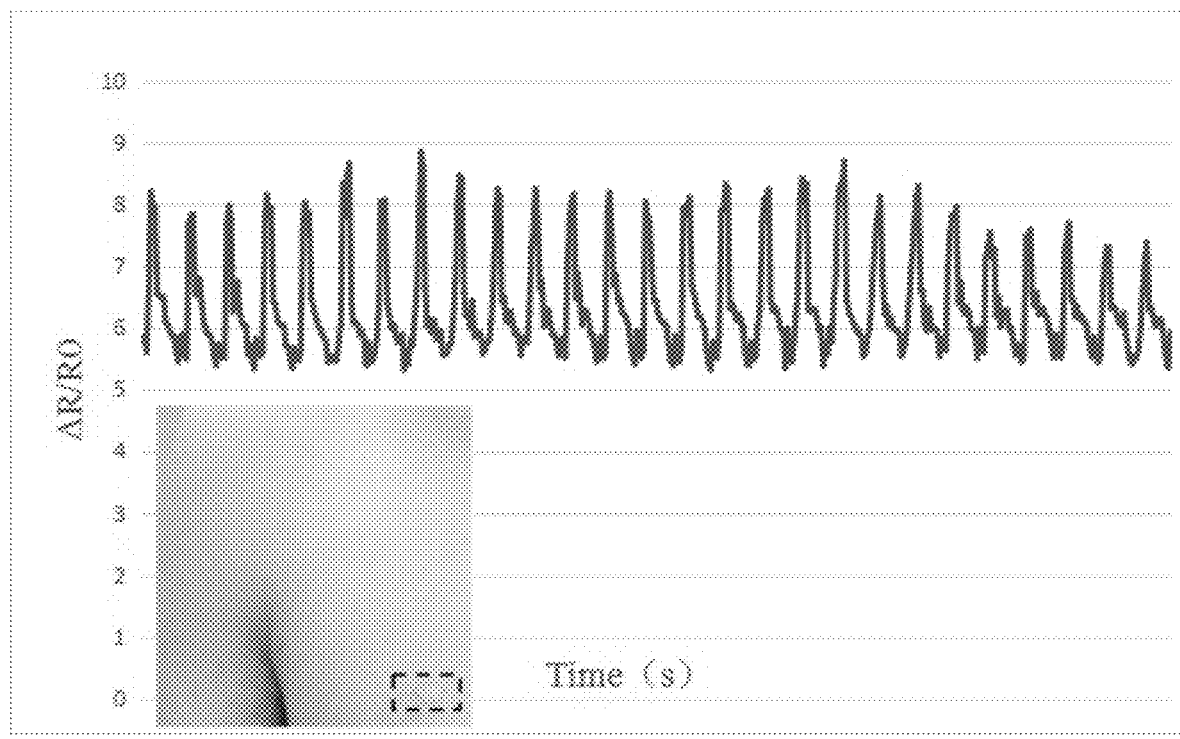
FIG. 5 is a schematic diagram showing human breathing signal detection according to an embodiment of this application.

As shown in FIG. 5, the microcrack sensor sample sheet was attached to the chest of a test subject, and two ends of the sample sheet are connected to a Keysight 34465A multimeter to detect real-time changes in resistance with the breathing of the test subject.

Breathing is one of the most important physiological signals for human bodies. Information conveyed by breathing can largely reflect a person's physiological health status. For example, a person's breathing during a surgical operation can reflect the physiological status of the human body in real time, and detecting a person's breathing data during sleep can be used as an important basis for measuring the sleep quality of the human body. The principle that the microcrack sensing element can sensitively detect breathing signals of the human body is similar to the stretching experiment. When the human body breathes, the chest cavity will expand with the inhalation and contract with the exhalation. Accordingly, the microcrack sensing element closely attached to the chest is subjected to tensile strain, resulting in a drastic change in resistance. Based on the excellent performance of the flexible microcrack-based strain sensing element, the resistance of the sensor can change significantly during breathing of the human body. A resistance value of the microcrack sensing element in the breathing process of the human body is recorded at a fixed frequency. The recorded resistance data is processed through relative resistance ($\Delta R/R0$) calculation to obtain a breathing waveform with time as the abscissa. A physiological condition or sleep quality of the human body during the recording period may be analyzed according to the waveform.

Figure 6:
FIG. 6 is a schematic diagram showing a human pulse signal experiment according to an embodiment of this application.
Figure 7:
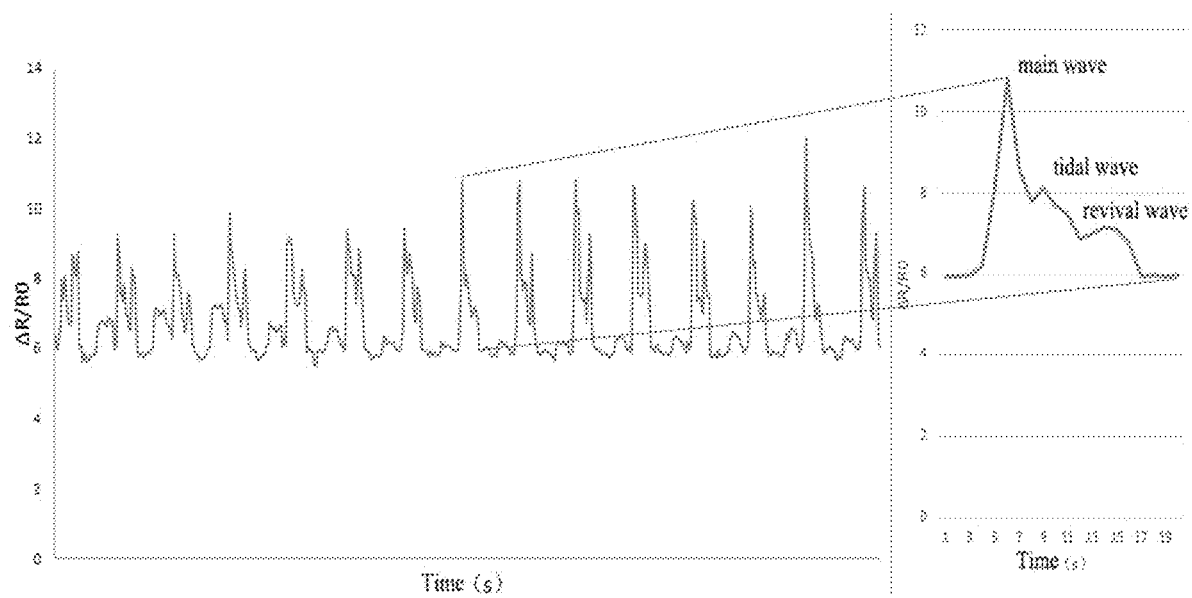
FIG. 7 is a schematic waveform diagram of human pulse signal detection according to an embodiment of this application.

The microcrack-based strain sensing element is attached to a wrist of the test subject, as shown in FIG. 6. Two ends of the microcrack-based strain sensing element are connected to a Keysight 34465A multimeter to detect a waveform generated by the change of the relative resistance of the sensor with the pulse signal of the human body, as shown in FIG. 7. A complete pulse cycle is obtained from the waveform. Based on the excellent sensitivity of the flexible microcrack-based strain sensing element, three stages of the pulse waveform in one cycle can be clearly distinguished from the curve: main wave, tidal wave, and revival wave, as shown in FIG. 7.

Then, the inputted resistance data of the flexible microcrack sensing element is processed in real time using a preprogrammed software program to calculate relative resistance data, so as to output a pulse detection curve with time as the abscissa in real time, where a main wave, a tidal wave, and a revival wave. Therefore, the flexible microcrack sensor has excellent performance and can reflect a patient's heart rate during clinical surgery in real time, so as to determine the patient's physiological condition. This lays a solid foundation for the use of the microcrack-based strain sensor in future smart medical devices.

Apparently, the above-described embodiments are merely examples provided for clarity of description, and are not intended to limit the implementations of the invention. Other variations or changes can be made by those skilled in the art based on the above description. The embodiments are not exhaustive herein. Obvious variations or changes derived therefrom also fall within the protection scope of the invention.

What is claimed is:
1. A method for preparing a microcrack-based strain sensing element, comprising steps of:
  (1) fabricating a coating template with a corresponding hollow shape according to a shape of a required sensing element, placing the coating template on a substrate layer, and coating a metal film layer formed by deposition of two metal materials on the substrate layer;
  (2) fabricating a protective layer template with a pattern of the corresponding hollow shape according to a required crack density and position, and spray-coating a release agent;
  (3) fixing the protective layer template to a surface of the metal film layer, and brush-coating a raw material of a protective layer on the protective layer template;
  (4) demolding after curing of the protective layer, and arranging an output electrode to obtain a sample sheet;
  (5) spin-coating a raw material of a packaging layer on a surface of the sample sheet; and
  (6) bending and stretching the metal film layer to obtain a patterned crack structure on a surface of the metal film layer, wherein the microcrack-based strain sensing element, comprising:

the substrate layer;

the metal film provided on the substrate layer, wherein the metal film is formed by deposition of two metal materials, and the metal film is provided with a patterned crack structure;

the protective layer provided on the metal film;

the output electrode connected to the metal film and configured to output an electrical signal; and the packaging layer provided on the protective layer.

2. The method according to claim 1, wherein the coating template comprises a hollow part, and two ends of the hollow part are each provided with a protruding part.

3. The method according to claim 1, wherein the protective layer template comprises rectangular hollow grooves spaced apart from each other.

4. The method according to claim 1, wherein the patterned crack structure is an array of cracks on the surface of the metal film layer, and the cracks are located between the protective layers arranged at intervals on the surface of the metal film layer.

5. The method according to claim 1, wherein the substrate layer is selected from a film of a polyimide, polyethylene terephthalate, polyvinyl chloride, nylon, or cast polypropylene material.

6. The method according to claim 1, wherein the metal film layer is a film formed by deposition of a metal film and a chromium phase, and the metal film is selected from the group consisting of a gold film, a platinum film, a silver film, and a copper film.

7. The method according to claim 1, wherein a raw material of the protective layer is prepared by mixing and stirring an epoxy resin A glue and an epoxy resin B glue at a weight ratio of 3:1.

8. The method according to claim 1, wherein a raw material of the packaging layer is prepared by mixing and stirring a polydimethylsiloxane sample liquid with water at a weight ratio of 10:1.

* * * * *